(12) United States Patent
Otts

(10) Patent No.: US 9,505,563 B2
(45) Date of Patent: Nov. 29, 2016

(54) DISC LANE GATE FUNCTION

(71) Applicant: Beckman Coulter, Inc., Brea, CA (US)

(72) Inventor: Stephen L. Otts, Brownsburg, IN (US)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 14/820,134

(22) Filed: Aug. 6, 2015

(65) Prior Publication Data

US 2016/0039615 A1 Feb. 11, 2016

Related U.S. Application Data

(60) Provisional application No. 62/033,973, filed on Aug. 6, 2014.

(51) Int. Cl.
| | | |
|---|---|---|
| *B65G 47/71* | (2006.01) | |
| *B65G 47/82* | (2006.01) | |
| *G01N 35/04* | (2006.01) | |

(52) U.S. Cl.
CPC ............... *B65G 47/71* (2013.01); *B65G 47/82* (2013.01); *G01N 35/04* (2013.01); *B65G 2201/0261* (2013.01); *G01N 2035/0467* (2013.01); *G01N 2035/0472* (2013.01)

(58) Field of Classification Search
CPC .............. B65G 47/71; B65G 47/82; B65G 2201/0261; B65G 47/846; B65G 2047/68; G01N 35/04; G01N 2035/0472; G01N 2035/0467
USPC ....... 198/367, 367.1, 368, 440, 441, 457.07, 198/458, 459.2, 459.6, 459.7
See application file for complete search history.

(56) References Cited

U.S. PATENT DOCUMENTS

| | | | | |
|---|---|---|---|---|
| 2,602,531 | A | | 7/1952 | Plank |
| 2,827,998 | A | * | 3/1958 | Breeback ............... B65G 47/71 198/441 |
| 3,613,885 | A | * | 10/1971 | Rehse ................... B07C 5/3412 209/528 |

(Continued)

FOREIGN PATENT DOCUMENTS

| | | |
|---|---|---|
| DE | 20 2010 017 525 U1 | 1/2012 |
| EP | 0 916 952 A2 | 5/1999 |

(Continued)

OTHER PUBLICATIONS

International Search Report and Written Opinion mailed on Oct. 21, 2015 for PCT Patent Application No. PCT/US2015/044081, 12 pages.

*Primary Examiner* — Mark A Deuble
(74) *Attorney, Agent, or Firm* — Kilpatrick Townsend & Stockton LLP

(57) ABSTRACT

Embodiments of the invention are directed to a transfer apparatus and a transport system which may be used in automated medical laboratory in-vitro diagnostic systems for handling patient samples. The transfer apparatus an embodiment of the invention comprises a rotatable disc and a lane gate. The transport system according to an embodiment of the invention comprises a transfer path arrangement including at least a first input lane and two output lanes at the transfer apparatus (i.e., the rotatable disc and the lane gate). The rotatable disc and the lane gate are cooperatively structured to function together to move at least one laboratory product transport element between the at least one input lane and the two output lanes of the transport system. The laboratory product transport element transports laboratory products, such as patient samples.

24 Claims, 9 Drawing Sheets

(56) References Cited

U.S. PATENT DOCUMENTS

| | | | | |
|---|---|---|---|---|
| 3,717,239 A | * | 2/1973 | Carter | B65G 47/71 198/374 |
| 3,967,717 A | * | 7/1976 | Bauer | B65G 47/71 198/441 |
| 5,941,366 A | * | 8/1999 | Quinlan | B65G 17/002 198/465.1 |
| 6,024,204 A | * | 2/2000 | van Dyke, Jr. | G01N 35/04 198/379 |
| 6,202,829 B1 | * | 3/2001 | van Dyke, Jr. | G01N 35/04 198/349.6 |
| 6,520,313 B1 | * | 2/2003 | Kaarakainen | B65G 35/06 198/358 |
| 8,701,863 B2 | * | 4/2014 | Abbestam | 198/370.01 |
| 9,248,980 B2 | * | 2/2016 | Pedrazzini | B65G 47/46 |
| 2005/0207937 A1 | | 9/2005 | Itoh | |
| 2013/0125675 A1 | * | 5/2013 | Muller | B01D 21/262 73/864.23 |

FOREIGN PATENT DOCUMENTS

| | | |
|---|---|---|
| EP | 1 106 542 A1 | 6/2001 |
| WO | 2009/035391 A1 | 3/2009 |
| WO | 2012/071008 A1 | 5/2012 |

* cited by examiner

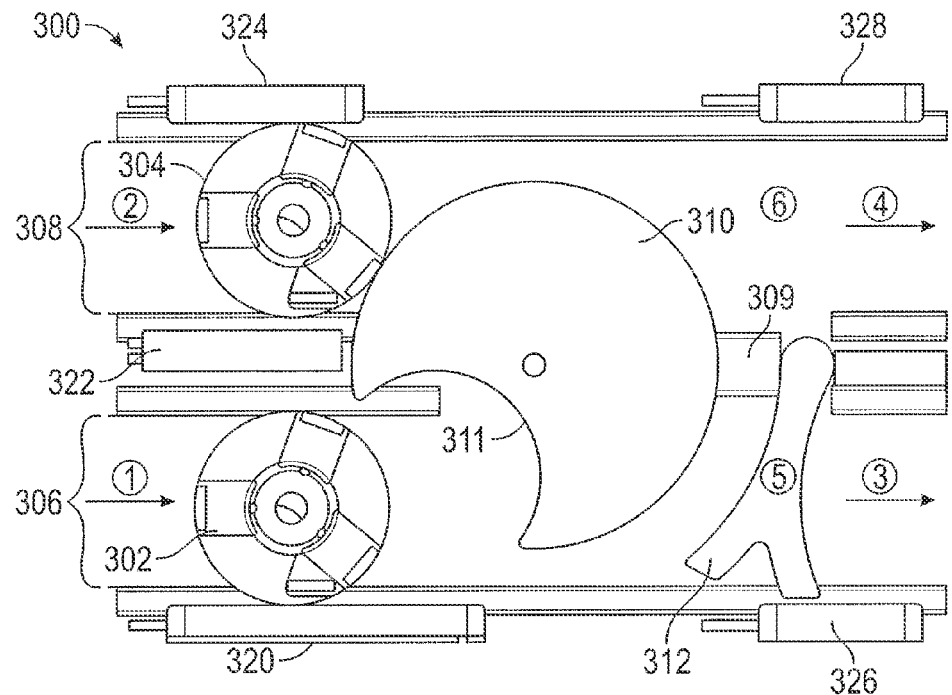
FIG. 3A
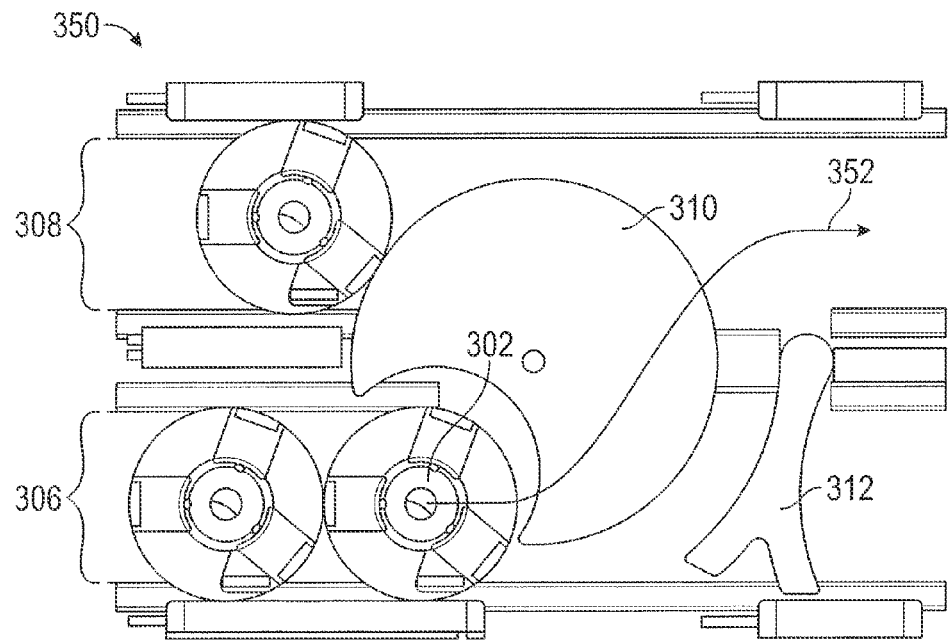
FIG. 3B1

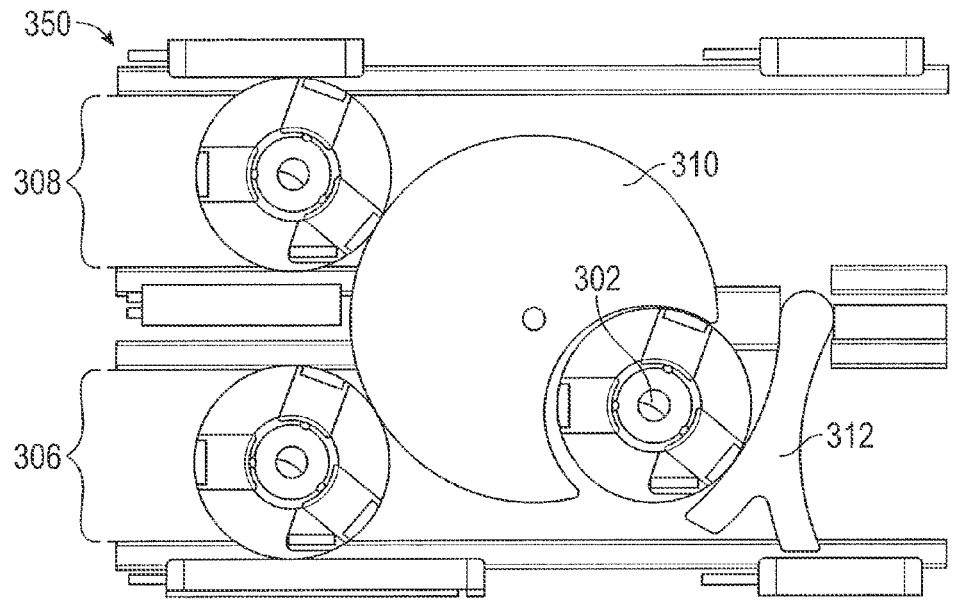
FIG. 3B2
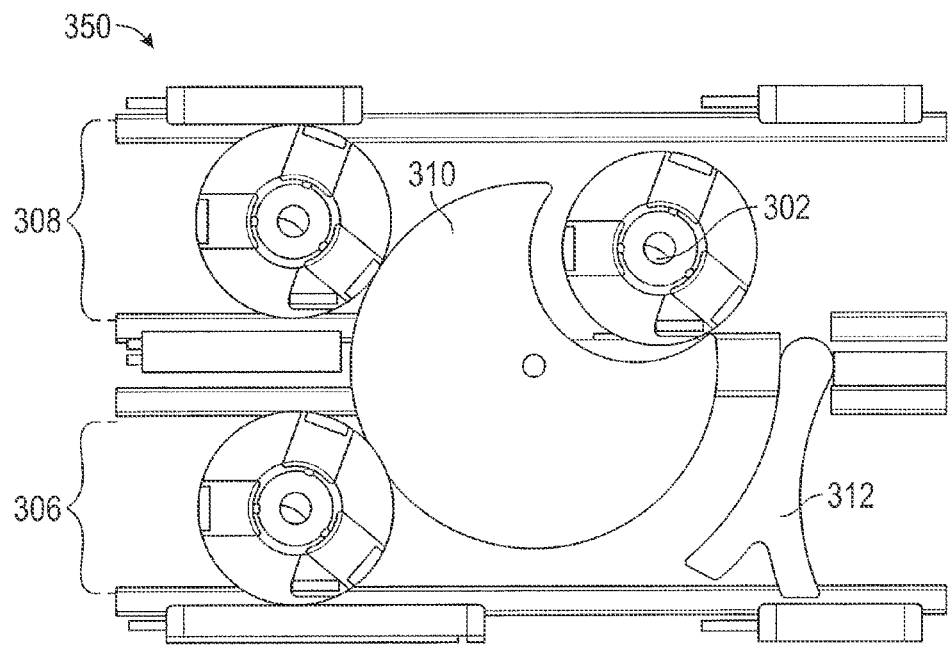
FIG. 3B3

DISC LANE GATE FUNCTION

RELATED APPLICATIONS

This application claims the benefit of and priority to U.S. Provisional Application No. 62/033,973, filed Aug. 6, 2014 and entitled "DISC LANE GATE FUNCTION," the entire disclosure of which is incorporated herein by reference for all purposes.

BACKGROUND

Laboratory transport systems such as gripper or conveyor systems are used in medical laboratories to transport sample tubes from one processing station to another processing station. Such sample tubes may comprise laboratory samples including, but not limited to, a sample fluid such as blood, and the sample fluid can be processed for chemical, biological or physical examination.

Individual tubes in the known systems are transported by means of laboratory product transport elements which are moved on a transport system. It may be desirable to move the laboratory product transport elements from an input transport lane to an output transport lane. However, during the transfer of a transport element from an input lane to an output lane, the transport element may be subject to vibrations, which may lead to perturbation of the transported sample materials. This is often detrimental for subsequent processing steps of the sample materials such as the aliquotation of a centrifuged blood sample may no longer be possible if the liquid and solid material layers, established by centrifugation, are disrupted. For example, in a conveyor based transportation systems, a transport element can be moved from a first lane to a second lane using a stop flipper system.

An exemplary stop flipper system 100 is illustrated in FIG. 1. The laboratory product transport elements 102 and 104 traveling on a first lane 108 need to be transported to a second lane 106. The illustrated stop flipper system 100 employs a flipper arm 112 that guides the laboratory product transport element 104 through an opening 116 provided between the two lanes 106 and 108. When a portion of the laboratory product transport element 104 is on the flipper arm 112, flipper arm 112 moves up toward the second lane 106. The movement of the flipper arm 112 moves the laboratory product transport element 104 toward the second lane 106 through the opening 116. A stopper arm 110 may be provided to stop any subsequent laboratory product transport elements, such as laboratory product transport element 102, from moving forward on the first lane 108. When the flipper arm 112 is in a neutral position, i.e. between the two lanes 106 and 108, the laboratory product transport elements travel forward on the first lane 108.

The stop flipper design discussed above results in singulation issues where a plurality of laboratory product transport elements pass before a laboratory product transport element can be picked and transferred from the first lane to the second lane. As such, it is ineffective to use the stop flipper design for systems where specific (e.g., predetermined) laboratory product transport elements should be transferred between transport lanes. In addition, the stop flipper design yields a maximum throughput of about 2400 tubes per hour ("TPH"). This throughput is considered to be low for a system where the goal is to achieve a throughput of about 2800 TPH. Moreover, in the stop flipper system 100 illustrated in FIG. 1, the second lane 106 moves in a direction opposite to the moving direction of the first lane 108. Thus, there is a need to reliably move the laboratory product transport elements between two same direction lanes of a transport system.

Additional drawbacks of some conventional systems result in the laboratory product transport elements dipping down between the lanes and, thus, causing motion errors due to the flipper arm only pushing at a tangential point to the laboratory product transport element.

Furthermore, conventional systems are not suited to handle orientation-specific laboratory product (i.e. sample) transport elements (i.e. orientation-specific laboratory product transport element). An orientation-specific laboratory product transport element has a dedicated front portion and a back portion. The front portion of the orientation-specific laboratory product transport element stays aligned with the moving direction of the transport element during transport by having, for example, the structural features of the transport element to interface with structural features of the track upon which the transport element travels. In conventional systems, such as in a stop flipper system, an orientation-specific transport element may not be able to conduct a complete half-turn when the transport element is being transferred from a first lane moving into a first direction onto a second lane moving into an opposite direction. Thus, when the front portion of the orientation-specific laboratory product transport element is no longer aligned with the moving direction of the transport element, a jam on the respective lane may result.

The task of embodiments of the invention is to provide a laboratory transport system and methods for its operation which permits simple and reliable operation, reduce the amount of concussion inflicted to sensitive samples, and entail lower design demands. Embodiments of the invention address the foregoing and other problems, individually and collectively.

SUMMARY

Embodiments of the present invention relate to an apparatus and a laboratory transport system used in automated medical laboratory in-vitro diagnostic systems for handling patient samples. The apparatus according to an embodiment of the invention comprises a rotatable disc and a lane gate. The transport system according to an embodiment of the invention comprises a transfer path arrangement including at least a first input lane and two output lanes at the apparatus (i.e., the rotatable disc and the lane gate). The rotatable disc and the lane gate are cooperatively structured to function together to transfer at least one transport element between the at least one input lane and a selected one of the output lanes of the transport system. The transport element may, for example, transport laboratory products, such as patient samples.

Even though embodiments are described in connection with laboratory transport systems, the present invention is not limited to laboratory transportation. The present application is applicable in all situations where transport elements carrying individually manufactured items such as raw material samples, reagent bottles etc., are to be selectively guided in a multi-lane transportation system.

According to an exemplary embodiment, an apparatus for use with transport lanes includes a rotatable disc and a lane gate provided adjacent to the rotatable disc. The transport lanes include at least one input lane, a first output lane and a second output lane. The rotatable disc is provided between the first output lane and the second output lane. The rotatable disc includes at least one lateral opening interfaceable with a transport element traveling on the at least one input lane. An axis of rotation of the rotatable disc is perpendicular to a top surface of the first output lane and the second output lane. The lane gate is pivotable to block access of the transport element to the first output lane or the second output lane.

In some embodiments, a transport system is provided. The transport system includes a multi-lane transport arrangement, a rotatable disc, a lane gate provided adjacent to the rotatable disc and a controller. The multi-lane laboratory product transport arrangement includes at least one input lane, a first output lane and a second output lane. The rotatable disc provided at an end of the at least one input lane and at a beginning of the first output lane and the second output lane. The rotatable disc includes at least one lateral opening interfaceable with a transport element traveling on the at least one input lane. An axis of rotation of the rotatable disc is perpendicular to a top surface of the first output lane and the second output lane. The lane gate is pivotable to block access of the transport element to the first output lane or the second output lane depending on a pre-determined travel path of the laboratory product transport element. A controller programmed to control a movement of the rotatable disc and the lane gate in order to guide the transport element through the multi-lane transport along the pre-determined travel path.

According to an exemplary embodiment, a method is provided to control the movement of a transport element within a multi-lane transport system, the multi-lane transport system including at least first input lane, a first output lane, a second output lane, a rotatable disc with at least one lateral opening for receiving a transport element and a lane gate for selectively blocking access to the first or the second output lane. The method includes detecting the transport element on the at least one input lane. A lane gate is moved to block access to one of a first output lane and a second output lane. The method also includes rotating the rotatable disc to a position where the lateral opening of the rotatable disc faces the detected transport element; and receiving the detected transport element in the lateral opening of the rotatable disc. The rotatable disc is then rotated to align the transport element with the output lane which is not blocked by the lane gate. The transport element is released from the lateral opening of the rotatable disc to said output lane which is not blocked by the lane gate by virtue of the movement of said output lane.

These and other embodiments are described in further detail below.

BRIEF DESCRIPTION OF THE DRAWINGS

FIG. 3A shows two laboratory product transport elements provided on an exemplary transport system, according to an exemplary embodiment.

FIGS. 3B1-3B3 are a series of sequential figures illustrating the exemplary transport system moving an exemplary laboratory product transport element from a first lane to a second lane, according to an exemplary embodiment.

DETAILED DESCRIPTION

Figure 1:
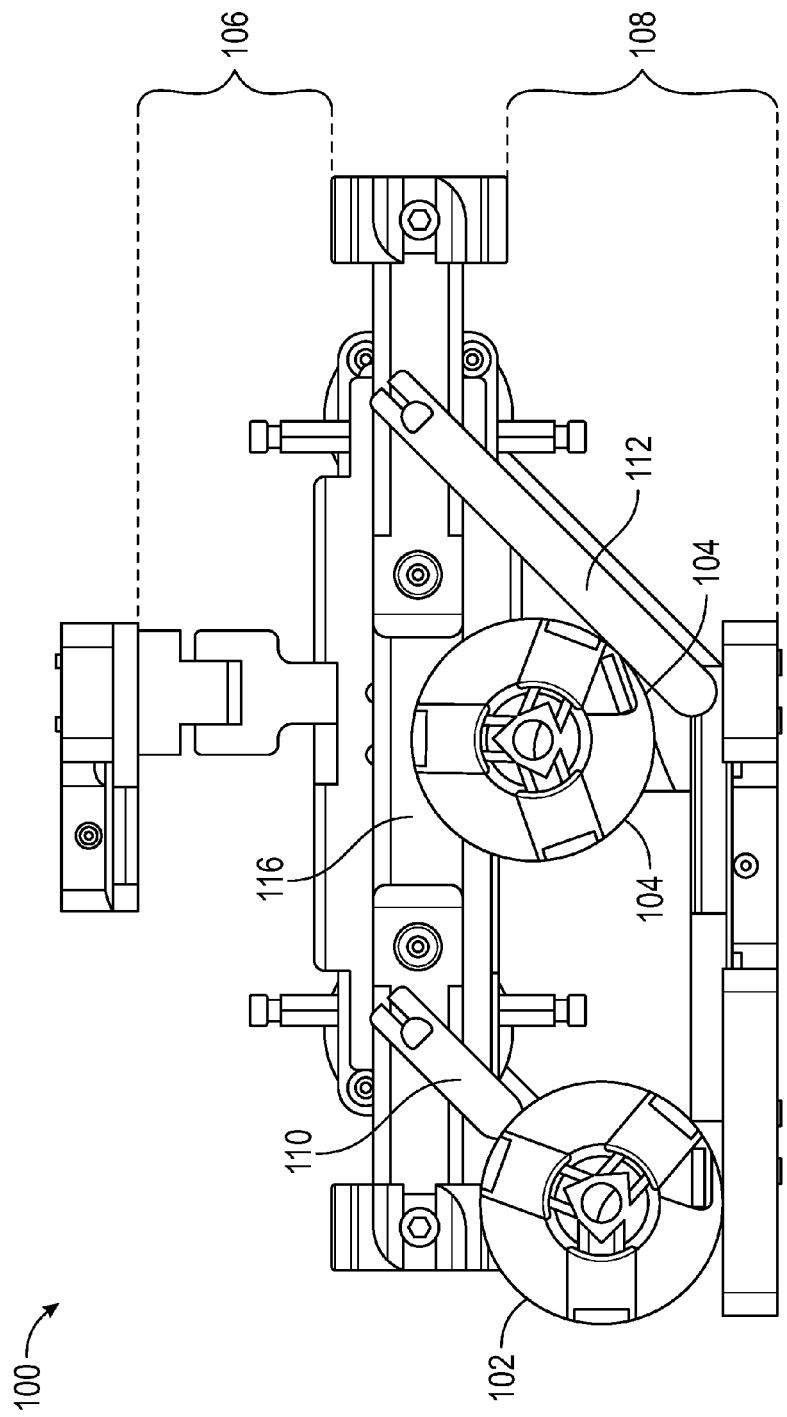
FIG. 1 shows a stop flipper transport mechanism.

The following detailed description may utilize terms as provided below to describe different aspects of different embodiments.

A "laboratory product" may refer to a variety of different containers that may be transported within a laboratory transport system. Examples of such containers include, but are not limited to, a test tube, a sample tube, a sample container, or any container that may be configured to hold a laboratory sample. In addition, a laboratory product may be capped or uncapped in different situations. Also, in some embodiments of the invention, the laboratory product may also be pre-centrifuged prior to being transported. The term "sample" is used herein interchangeably with the term "laboratory product".

A "laboratory product transport element" may include a variety of different transport elements configured to transport a laboratory product within a laboratory transport system. A laboratory product transport element can transport a laboratory product (e.g., a sample tube) using any suitable mode of transport. Exemplary laboratory product transport elements may include devices which facilitate movement of the element, such as wheels. Other exemplary laboratory product transport elements may not be capable of autonomous movement but may be passively transported on moving surfaces, e.g. conveyor lanes. The transport element can transport one or more laboratory products (e.g., a sample container with a sample in it). The terms "laboratory product transport element", "sample transport element", "transport element" and "carrier" are used interchangeably throughout the present application.

A "laboratory transport system" according to an embodiment of the invention can include at least one laboratory product transport element and a transfer path arrangement. A laboratory transport system may include a variety of different subsystems. For example, some laboratory transport systems may include a transfer path arrangement and one or more laboratory product transport elements. Some laboratory transport systems may be active transport systems, while others may be passive transport systems. An active transport system may include chain or belt conveyors upon which laboratory product transport elements are moved, or transport elements are moved along a path by magnetic attraction caused by one or more magnets that are moved along the pre-determined path. Passive transport systems utilize self-propelled transport elements that can avoid the use of chain or belt conveyors or movable magnets, and instead move along transfer surfaces utilizing different movement components that are part of the laboratory product transport element itself.

A "transfer path" may refer to a variety of different surfaces within a laboratory transport system upon which a laboratory product transport element may travel. In some cases, a transfer path may include a smooth surface. A transfer path may be part of a transfer path arrangement that may include one or more transfer paths along with other features in some cases. Suitable examples of transfer paths may include a horizontal web with side limitations (e.g., walls) which can confine the movement of a laboratory product transport element. In some cases, the transfer path may have a marker (e.g., a line) which can be followed by a laboratory product transport element. Transfer paths may head in one or more directions. Transfer paths may include one or more input lanes and one or more output lanes. In some embodiments, an input lane and an output lane may be formed as a continuous single lane. The lanes may include side limitations such as borders provided on each side of the lane. In some embodiments, there may be no border between directly adjacent lanes to allow the transport elements traveling on one lane to cross onto the adjacent lane.

A "transfer path arrangement" may include additional features, some of which may be active while others may be passive. A transfer path arrangement may include, but is not limited to, barriers, markers, indicators, discs, gates, sensors, transmitters, receivers, electrical conductors, sample gripping and/or analysis positions, power sources, electromagnetic radiation sources, and/or optical devices. A transfer path arrangement may be incorporated in an exemplary transport system.

A "sensor" may refer to a variety of different sensors configured to detect aspects or signals within a laboratory transport system. Sensors may include, but are not limited to: carrier detection sensors detecting the presence of the transport element on an input lane or an output lane; collision sensors configured to detect markers, obstacles, and/or other laboratory product transport elements; and reflective sensors configured to detect one or more position indicators. In some cases, sensors may include RFID readers and/or near-field communication devices.

An "energy source" may refer to a variety of sources of power for components of a laboratory transport system. Energy sources may include sources of drive power for one or more elements of the laboratory transport system. Energy sources may include an energy receiver and an energy accumulator in some cases. An energy accumulator may include, but is not limited to one or more batteries and/or fuel cells. Energy sources may also include, but are not limited to, voltage sources that may provide energy to a transfer path arrangement.

A "movement device" may refer to a variety of different components that a laboratory product transport element may utilize to move independently along a transfer path. A movement device may include, but is not limited to, a wheel, ball, etc.

A "drive device" may refer to a variety of different components that may drive elements of the laboratory transport system. A drive device may receive drive signals from a variety of different sources, including a control unit in some cases. A drive device may include, but is not limited to, different motors such as direct current electric motors.

A "laboratory product transport element" according to an embodiment of the invention has at least one holder to hold a laboratory product being transported. In some embodiments, the laboratory product transport element may be orientation-specific in that the orientation of the laboratory product transport element should be maintained while the laboratory product transport element is traveling on the transport system. The laboratory product transport element may be an active transport element and have an energy receiver and/or an energy accumulator to furnish drive power. At least one signal receiver serves to receive control signals, as a function of which a control unit can generate drive signals. Depending on the control signals, drive devices drive movement devices, with which the laboratory product transport element can independently move on a transfer path. The drive devices are operated with the drive power received from the energy receiver and/or stored in an energy accumulator of the laboratory product transport element.

An "energy receiver" can include any suitable device that is capable of receiving energy and is capable of providing such energy to a laboratory product transport element. Examples of energy receivers include an induction coil, a photosensitive element (e.g., a photovoltaic cell), a light receiver, a radio signal receiver, etc.

A "signal transmitter" may be any suitable device capable of transmitting a signal from a laboratory product transport element to an external signal receiver. Such signal transmitters can transmit signals using any suitable technology including optical, electrical and magnetic technologies. Examples of signal transmitters can include radio signal transmitters, infrared light transmitters, etc.

A "holder" in a laboratory product transport element may include structures suitable for securely holding a sample container (e.g., a tube) during transportation of the sample container. Exemplary holders may include structures such as housings that may be formed so that they are cooperatively structured with one or more sample containers. In some embodiments, a holder may hold only one laboratory product (e.g., only one sample tube with a sample in it).

Different laboratory product transport elements can be used, e.g. for transporting different laboratory products like containers of different sizes, containers with different types of samples, slides, etc.

The laboratory transport system according to an embodiment of the invention is particularly suited for transport of sample tubes in in-vitro diagnostic laboratories, especially for the transport of patient fluid samples between different portions of an in vitro diagnostic system.

Embodiments of the invention are directed to methods and systems for transporting a laboratory product (e.g. a clinical sample) transport element between at least one input lane and at least two output lanes. The input and output lanes may be movable conveyor lanes. More specifically, a lane gate and a rotatable disc are controlled to move at least one laboratory product transport element from a first input lane to a first output lane or a second output lane, depending on a pre-determined travel path of the laboratory product transport element. The lane gate is used to direct the travel of the laboratory product transport element by blocking access to an output lane to prevent the transport element from travelling on a travel path that is different from the pre-determined travel path. The lane gate may move simultaneously with rotation of the rotatable disc to transfer the laboratory product transport element to the correct lane. The transport element may or may not be orientation-specific, i.e. the transport element may maintain a certain orientation in relation to the transfer path while being transported along the transfer path.

The transport system may be an active transport system or a passive transport system. Active transport systems for moving the laboratory product transport elements from one station to the other include at least one movable conveyor lane upon which the laboratory product transport elements are positioned or another mechanism for pushing or pulling the laboratory product transport element along a pre-defined path. Examples of movable conveyor lanes include chain or belt conveyors. Each possible path is defined by a separate chain or belt conveyor. Passive transport systems utilize self-propelled transport elements that can avoid the use of chain or belt conveyors or movable magnets, and instead move along transfer surfaces utilizing different movement components that are part of the laboratory product transport element itself.

In various embodiments, only one laboratory product transport element is carried by the rotatable disc at a time. Other laboratory product transport elements moving on the lanes are held back using, for example, the rotatable disc. The rotatable disc includes a lateral opening for picking up the orientation-specific laboratory product transport element. The lateral opening may allow for better interfacing (e.g. coupling) between the rotatable disc and the laboratory product transport element. The rotatable disc is sized and dimensioned such that a laboratory product transport element, arriving at an input lane, is prevented from moving forward on either one of the first output lane or the second output lane unless the laboratory product transport element is placed in the at least one lateral opening of the rotatable disc. The laboratory product transport element is transferred to the appropriate output lane via rotation of the rotatable disc. For example, if the rotatable disc has a circular shape (with the exception of the at least one lateral opening), an additional transport elements, arriving at an input lane, will come into contact with the rotatable disc, but cannot proceed further, unless the rotatable is rotated such that the additional transport element can enter a lateral opening of the disc. Due to the circular shape of the disc a sample, held by the additional transport element which is waiting to be accepted into the lateral opening of the rotatable disc, will experience only minimal agitation when the rotatable disc is being rotated, e.g. in order to transport a first transport element to an output lane.

The rotatable disc may move clockwise or counter-clockwise to minimize or prevent the disturbance of the sample carried by the transport element. In some embodiments, a programmable logic (e.g. a controller) may control the movement of the rotatable disc and the lane gate. For example, in a system with two input lanes and two output lanes, a transport element arriving at the first input lane will not be transported past the second input lane when a second transport element is waiting at the second input lane. In order to avoid disturbance of the second transport element, the rotatable disc rotates in a direction that avoids the second transport element. In addition, the lane gate will be controlled such that the transport element is blocked from taking an exit into an output lane that does not correspond to a pre-determined travel path of the transport element.

Embodiments of the present application allow to achieve a throughput of at least 2800 TPH, even when every laboratory product transport element is crossed over from a first input lane to a second output lane. Thus, embodiments provide a fast and reliable transport of laboratory product transport elements between lanes while maintaining sample integrity.

Figure 2:
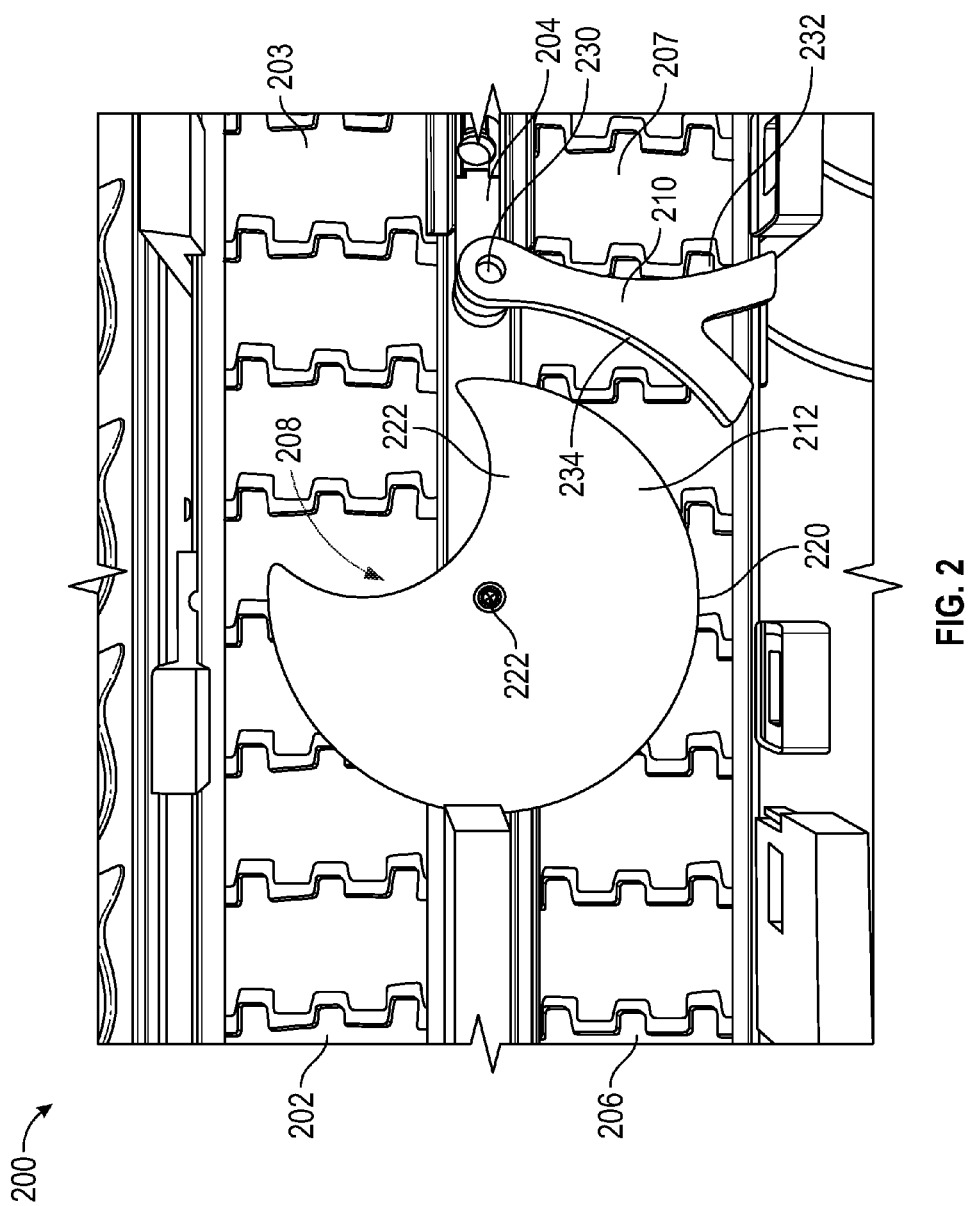
FIG. 2 shows an exemplary transport system including two continuous lanes, moving in the same direction, a rotatable disc and a lane gate, according to an exemplary embodiment.

FIG. 2 illustrates an exemplary transport system 200 including a first input lane 202, a second input lane 206, a first output lane 203 and a second output lane 207. The first input lane 202 and the first output lane 203 may be formed continuously as a single lane. The second input lane 206 and the second output lane 207 may be formed continuously as a single lane. The first input lane 202, the second input lane 206, the first output lane 203 and the second output lane 207 may be movable conveyor lanes such as chains or belt conveyors. For example, in the exemplary configuration illustrated in FIG. 2, the first input lane 202, the second input lane 206, the first output lane 203 and the second output lane 207 may move from left to right.

The exemplary transport system 200 may also include a cross-over bridge 204, a rotatable disc 212 and a lane gate 210, according to an exemplary embodiment. The rotatable disc 212 and the lane gate 210 may form a transfer apparatus.

The rotatable disc 212 may include at least one lateral opening 208. In some embodiments, the rotatable disc 212 may include a plurality of lateral openings provided at pre-determined angles with respect to the axis of rotation 224. For example, the rotatable disc 212 may include two lateral openings provided at pre-determined angles with respect to the axis of rotation 224. The lateral opening 208 may include a cut-out formed on the rotatable disc 212. For example, the cut-out may be a semi-circle cut-out creating an inner surface 222 with a negative curvature. As illustrated in FIG. 2, the rotatable disc 212 may have an outer surface 220 with a positive curvature and an inner surface 222 with a negative curvature, i.e. the lateral opening 208 forms a concave inner surface 222 on the rotatable disc. When the rotatable disc 212 couples with a laboratory product transport element traveling on the first input lane 202 or the second input lane 206, the opening 208 (i.e. the inner surface 222 of the rotatable disc 212) may interface with the laboratory product transport element. The semi-circle cut-out shape for the lateral opening is provided for illustration purposes only and should not be construed as limiting. The lateral opening may have any shape and dimension, e.g. an at least partially circular or rectangular shape that is suitable to interface with the laboratory product transport element.

The rotatable disc 212 may move the laboratory product transport element by rotating clockwise or counter-clockwise around an axis of rotation 224, depending on the initial moving direction of the laboratory product transport element. Accordingly, the rotatable disc 212 may carry the laboratory product transport element without disturbing the sample (i.e. laboratory product) carried by the laboratory product transport element. The axis of rotation 224 of the rotatable disc 212 may be perpendicular to top surfaces of the first input lane 202, the second input lane 206, the first output lane 203 and the second output lane 205.

The rotatable disc 212 may rotate at a first speed when moving a laboratory product transport element and at a second speed, faster than the first speed, when not moving the laboratory product transport element. The maximum speed for the rotatable disc 212 when moving a laboratory product transport element may depend on the sample type carried by the laboratory product transport element.

The lane gate 210 is provided adjacent to the rotatable disc 212. Specifically, the lane gate 210 is provided downstream from (i.e. after) the rotatable disc 212, in a moving direction of a laboratory transport element arriving on an input lane 202 or 206. The lane gate can have any configuration suitable for selectively blocking access of a carrier being transported within the rotatable disc to either a first or a second output lane 203 and 207. In the exemplary embodiment illustrated in FIG. 2, the lane gate 210 may have a Y-shape with two elongated side sections 232 and 234. The lane gate 210 may be cooperatively structured with the rotatable disc 212 such that the two elongated side sections 232 and 234 may have a negative curvature that corresponds to the positive curvature of the outer surface 220 of the rotatable disc 212. The corresponding curvatures cooperate such that a transport element (that is being transported within the rotatable disc past a first output lane blocked by the lane gate) can smoothly glide along the face of the lane gate (which is turned towards the rotatable disc) towards a second output pathway which is not blocked by the lane gate.

The lane gate 210 is pivotable about a pivot 230. In some embodiments, the lane gate 210 may be provided at a higher position than the rotatable disc 212. That is, a distance between the top surface of the transport lanes and the lane gate may be larger than a distance between the top surface of the transport lanes and the rotatable disc. In such embodiments, the lane gate 210 may pivot above the rotatable disc 212. In other embodiments, the lane gate 210 may be provided at a lower position than the rotatable disc 212. That is, a distance between the top surface of the transport lanes and the lane gate may be smaller than a distance between the top surface of the transport lanes and the rotatable disc. In such embodiments, the lane gate 210 may pivot below the rotatable disc 212. One of ordinary skill in the art will appreciate that the lane gate 210 may be provided at the same level as the rotatable disc 212 if enough distance is provided there between such that the lane gate 210 is pivotable without colliding with the rotatable disc 212. Alternatively, the lane gate 210 may be provided at the same level as the rotatable disc 212 and the lane gate 210 may pivot away from the rotatable disc 212 to prevent collision with the rotatable disc 212.

When a laboratory sample transport element is provided at the first input lane 202 or the second input lane 206, the lane gate 210 may pivot to block access of the laboratory sample transport element to the first output lane 203 or the second output lane 207. Accordingly, the lane gate 210 may direct the travel path of the laboratory product transport element. Specifically, the lane gate 210 directs the laboratory product transport element in a pre-determined travel path by blocking either first output lane 203 or the second output lane 207 (as illustrated in the FIG. 2). According to various embodiments, the lane gate 210 may move substantially simultaneously with the rotatable disc 212.

The lane gate 210 is pivotable about an axis that may be parallel to the axis of rotation of the rotatable disc 212. The lane gate 210 may be positioned downstream from the rotatable disc 212 (with regard to the travel direction of the transport elements) and between a first output lane 203 and a second output lane 207. The lane gate 210 may be configured to block the access to the first output lane 203 when the lane gate 210 is at a first position, to block the access to the second output lane 207 when the lane gate 210 is at a second position and to block the access to neither the first output lane 203 nor the second output lane 207 when the lane gate 210 is at a third position. According to embodiments of the invention, transport systems may comprise multiple lane gates. For example, in case of a multi-lane transport arrangement having two input lanes and four output lanes, a first lane gate may be operative to selectively block access to either a first output lane or a second output lane, while a second lane gate may be operative to selectively block access to either a third output lane or a fourth output lane.

The movement of the lane gate and the rotatable disc to transfer a laboratory product transport element from a two-lane input pathway to a two-lane output pathway will be described in connection with FIGS. 3A-3B3.

FIG. 3A illustrates two laboratory product transport elements 302, 304 provided on an exemplary transport system 300. The exemplary transport system 300 may include movable conveyor lanes such as a first movable continuous conveyor lane 306 and a second movable continuous conveyor lane 308. For example, a first input lane and a first output lane may be formed as the first movable continuous conveyor lane 306. A second input lane and a second output lane may be formed as the second movable continuous conveyor lane 308. In some embodiments, the first movable continuous conveyor lane 306 may be parallel to the second movable continuous conveyor lane 308.

The exemplary transport system 300 may also include a transfer apparatus comprising a rotatable disc 310 and a lane gate 312. The first movable continuous conveyor lane 306 and the second movable continuous conveyor lane 308 may extend below the rotatable disc 310. A diameter of the rotatable disc 310 may be equal to a combined width of the first movable continuous conveyor lane 306 and the second movable continuous conveyor lane 308.

In the exemplary embodiment illustrated in FIG. 3A, a first laboratory product transport element 302 traveling on the first movable continuous conveyor lane 306 arrives at a first position, position 1. A transport element presence sensor (e.g. a thru beam sensor or RFID sensor) 320 provided in proximity of position 1 may detect the arrival of the first laboratory product transport element 302. A second laboratory product transport element 304 traveling on the second movable continuous conveyor lane 308 arrives at a second position, position 2. A transport element presence sensor (e.g. a thru beam sensor or RFID sensor) 322 provided in proximity of position 2 may detect the arrival of the second laboratory product transport element 304.

Regarding the first laboratory product transport element 302, it is determined, for example by a control logic, whether the first laboratory product transport element 302 should continue traveling on the first movable continuous conveyor lane 306 or should be moved to the second movable continuous conveyor lane 308. If it is determined that the first laboratory product transport element 302 should continue traveling on the first movable continuous conveyor lane 306, the lane gate 312 is moved to position 6 to block access to the second movable continuous conveyor lane 308. Alternatively, the lane gate 312 may be moved to a neutral position in order to allow continued travel of the first laboratory product transport element 302 on the first movable continuous conveyor lane 306. The lane gate 312 may pivot over or below the rotatable disc 310, either clockwise or counter-clockwise.

The rotatable disc 310 is rotated into a position where the first laboratory product transport element 302 can enter the opening 311, for example by means of the movement of the first movable continuous conveyor lane 306. The first laboratory product transport element 302 may interact with the rotatable disc 310 in such a way that the first laboratory product transport element 302 does not protrude over the periphery of the rotatable disc 310 to be in physical contact with the outer borders of the movable conveyor lanes. In some embodiments, the rotatable disc 310 may be rotated substantially simultaneously with the movement of the lane gate 312.

The rotatable disc 310 may transport the first laboratory product transport element 302 to position 3 by rotating counter-clockwise. This way, the rotatable disc 310 may avoid a collision between the first transport element 302 and the second transport element 304 which could lead to a perturbation of sample contained in the respective transport elements. As soon as the rotatable disc 310 has been rotated to have the opening 311 facing onto position 3, the first laboratory product transport element 302 being transported in the opening 311, can leave the rotatable disc, for example by means of the movement of the first movable continuous conveyor lane 306. The first laboratory product transport element 302 may continue to move on the first movable continuous conveyor lane 306 as the lane gate is not in position 5 and therefore not blocking access to the first movable continuous conveyor lane 306.

Accordingly, when the first laboratory product transport element 302 is aligned with the first movable continuous conveyor lane 306 at position 3, the rotatable disc 310 releases the laboratory product transport element 302 on the first movable continuous conveyor lane 306. In some embodiments, an outer border of the first movable continuous conveyor lane 306 may continue (either straight or following the form of the rotatable disc 310) to guarantee that the first laboratory product transport element 302 cannot leave the rotatable disc 310 before the laboratory product transport element 302 arrives at a beginning of the first movable continuous conveyor lane 306.

Upon being released from the rotatable disc 310, the first laboratory product transport element 302 continues to travel on the first movable continuous conveyor lane 306. An exit sensor 326 provided in proximity of position 3 may detect that the first laboratory product transport element 302 is released from the rotatable disc 310. The rotatable disc 310 may sit idle at the position where the laboratory product transport element is released, i.e. position 3. The lane gate 312 may return to an idle position along a longitudinal axis of the cross-over bridge 309. Alternatively, the lane gate 312 may sit idle at position 6 until a next transport element need to be picked up by the rotatable disc 310.

If it is determined that the first laboratory product transport element 302 should be moved to the second movable continuous conveyor lane 308, the lane gate 312 is moved to position 5 (as illustrated in FIG. 3A) to block access to the first movable continuous conveyor lane 306. The movement 352 of first laboratory product transport element 302 according to this exemplary scenario 350 is illustrated in FIGS. 3B1-3B3.

The lane gate 312 may pivot over or below the rotatable disc 310 either clockwise or counter-clockwise to arrive at position 5. Alternatively, the lane gate 312 may be moved to a neutral position in order to allow continued travel of the first laboratory product transport element 302 on the first movable continuous conveyor lane 306. The rotatable disc 310 is rotated into a position where the first laboratory product transport element 302 can enter the opening 311, for example by means of the movement of the first movable continuous conveyor lane 306. The first laboratory product transport element 302 may interact with the rotatable disc 310 in such a way that the first laboratory product transport element 302 does not protrude over the periphery of the rotatable disc 310 to be in physical contact with the outer borders of the movable conveyor lanes. In some embodiments, the lane gate 312 may be moved substantially simultaneously with the rotation of the rotatable disc 310.

FIG. 3B1 illustrates the rotatable disc 310 accepts the first laboratory product transport element 302 in the opening 311. The rotatable disc 310 may transport the first laboratory product transport element 302 to position 4 by rotating counter-clockwise. This way, the rotatable disc 310 may avoid a collision between the first transport element 302 and the second transport element 304 which could lead to a perturbation of sample contained in the respective transport elements. As soon as the rotatable disc 310 has been rotated to have the opening 311 facing onto position 4, the first laboratory product transport element 302 being transported in the opening 311, can leave the rotatable disc, for example by means of the movement of the second movable continuous conveyor lane 308. The first laboratory product transport element 302 may continue to move on the second movable continuous conveyor lane 308 as the lane gate is not in position 6 and therefore not blocking access to the second movable continuous conveyor lane 308.

As illustrated in FIG. 3B2, during the rotation, the opening 311 of the rotatable disc 310 passes by position 3. However, since access to the first movable continuous conveyor lane 306 is blocked by the lane gate 312 (now at position 5), the rotatable disc 310 does not release the first laboratory product transport element 302 at position 3.

When the first laboratory product transport element 302 is aligned with the second movable continuous conveyor lane 308 at position 4, the rotatable disc 310 releases the laboratory product transport element 302 on the second movable continuous conveyor lane 308. In some embodiments, an outer border of the second movable continuous conveyor lane 308 may continue (either straight or following the form of the rotatable disc 310) to guarantee that the first laboratory product transport element 302 cannot leave the rotatable disc 310 before the laboratory product transport element 302 arrives at a beginning of the second movable continuous conveyor lane 308. The lane gate 312 may function as a flexible extension of the outer border of the first movable continuous conveyor lane 306 in order to smoothly guide the first laboratory product transport element 302 past a blocked lane, i.e. the first movable continuous conveyor lane 306.

Upon being released from the rotatable disc 310, the first laboratory product transport element 302 continues to travel on the second movable continuous conveyor lane 308. An exit sensor 328 provided in proximity of position 4 may detect that the first laboratory product transport element 302 is released from the rotatable disc 310. The rotatable disc 310 may sit idle at the position where the laboratory product transport element is released, i.e. position 4. The lane gate 312 may return to an idle position along a longitudinal axis of the cross-over bridge 309. Alternatively, the lane gate 312 may sit idle at position 5 until a next transport element need to be picked up by the rotatable disc 310.

Referring back to FIG. 3A, regarding the second laboratory product transport element 304, it is determined, for example by the control logic, whether the second laboratory product transport element 304 should continue traveling on the second movable conveyor lane 308 or should be moved to the first movable continuous conveyor lane 306. If it is determined that the second laboratory product transport element 304 should continue traveling on the second movable continuous conveyor lane 308, the lane gate 312 is moved to position 5 (as illustrated in FIG. 3A) to block access to the first movable continuous conveyor lane 306. Alternatively, the lane gate 312 may be moved to a neutral position in order to allow continued travel of the second laboratory product transport element 304 on the second movable continuous conveyor lane 308. The lane gate 312 may pivot over or below the rotatable disc 310, either clockwise or counter-clockwise to arrive at position 5.

The rotatable disc 310 is rotated into a position where the second laboratory product transport element 304 can enter the opening 311, for example by means of the movement of the second movable continuous conveyor lane 308. The second laboratory product transport element 304 may interact with the rotatable disc 310 in such a way that the second laboratory product transport element 304 does not protrude over the periphery of the rotatable disc 310 to be in physical contact with the outer borders of the movable conveyor lanes. In some embodiments, the lane gate 312 may be moved substantially simultaneously with the rotation of the rotatable disc 310.

The rotatable disc 310 may transport the second laboratory product transport element 304 to position 4 by rotating clockwise. This way, the rotatable disc 310 may avoid a collision between the second transport element 304 and the first transport element 302 which could lead to a perturbation of sample contained in the respective transport elements. As soon as the rotatable disc 310 has been rotated to have the opening 311 facing onto position 4, the second laboratory product transport element 304 being transported in the opening 311 can leave the rotatable disc, for example by means of the movement of the second movable continuous conveyor lane 308. The second laboratory product transport element 304 may continue to move on the second movable continuous conveyor lane 308 as the lane gate 312 is not in position 5 and therefore not blocking access to the first movable continuous conveyor lane 306.

Accordingly, when second laboratory product transport element 304 is aligned with the second movable continuous conveyor lane 308 at position 4, the rotatable disc 310 releases the second laboratory product transport element 304 on the second laboratory product transport element 304. In some embodiments, an outer border of the second laboratory product transport element 304 may continue (either straight or following the form of the rotatable disc 310) to guarantee that the second laboratory product transport element 304 cannot leave the rotatable disc 310 before the second laboratory product transport element 304 arrives at a beginning of the second movable continuous conveyor lane 308.

Upon being released from the rotatable disc 310, the second laboratory product transport element 304 continues to travel on the second movable continuous conveyor lane 308. An exit sensor 328 provided in proximity of position 4 may detect that the second laboratory product transport element 304 is released from the rotatable disc 310. The rotatable disc 310 may sit idle at the position where the laboratory product transport element is released, i.e. position 4. The lane gate 312 may return to an idle position along a longitudinal axis of the cross-over bridge 309. Alternatively, the lane gate 312 may sit idle at position 5 until a next transport element need to be picked up by the rotatable disc 310.

If it is determined that the second laboratory product transport element 304 should be moved to the first movable continuous conveyor lane 306, the lane gate 312 is moved to position 6 to block access to the second movable continuous conveyor lane 308. Alternatively, the lane gate 312 may be moved to a neutral position in order to allow continued travel of second laboratory product transport element 304 on the first movable continuous conveyor lane 306. The lane gate 312 may pivot above or below the rotatable disc 310 either clockwise or counter-clockwise to arrive at position 6. The rotatable disc 310 is rotated into a position where the second laboratory product transport element 304 can enter the opening 311, for example by means of the movement of the second movable continuous conveyor lane 308. The second laboratory product transport element 304 may interact with the rotatable disc 310 in such a way that the second laboratory product transport element 304 does not protrude over the periphery of the rotatable disc 310 to be in physical contact with the outer borders of the movable conveyor lanes. In some embodiments, the rotatable disc 310 may be rotated substantially simultaneously with the movement of the lane gate 312.

The rotatable disc 310 may transport the second laboratory product transport element 304 to position 3 by rotating clockwise. This way, the rotatable disc 310 may avoid a collision between the second transport element 304 and the first transport element 302 which could lead to a perturbation of sample contained in the respective transport elements. As soon as the rotatable disc 310 has been rotated to have the opening 311 facing onto position 3, the second laboratory product transport element 304 being transported in the opening 311, can leave the rotatable disc, for example by means of the movement of the first movable continuous conveyor lane 306. The second laboratory product transport element 304 may continue to move on the first movable continuous conveyor lane 306 as the lane gate is not in position 5 and therefore not blocking access to the first movable continuous conveyor lane 306.

Accordingly, when the second laboratory product transport element 304 is aligned with the first movable continuous conveyor lane 306 at position 3, the rotatable disc 310 releases the second laboratory product transport element 304 on the first movable continuous conveyor lane 306. In some embodiments, an outer border of the first movable continuous conveyor lane 306 may continue (either straight or following the form of the rotatable disc 310) to guarantee that the second laboratory product transport element 304 cannot leave the rotatable disc 310 before the second laboratory product transport element 304 arrives at a beginning of the first movable continuous conveyor lane 306. The lane gate 312 may function as a flexible extension of the outer border of the second movable continuous conveyor lane 308 in order to smoothly guide the second laboratory product transport element 304 past a blocked lane, i.e. the second movable continuous conveyor lane 308.

Upon being released from the rotatable disc 310, the second laboratory product transport element 304 continues to travel on the first movable continuous conveyor lane 306. An exit sensor 326 provided in proximity of position 3 may detect that the first laboratory product transport element 302 is released from the rotatable disc 310. The rotatable disc 310 may sit idle at the position where the laboratory product transport element is released, i.e. position 3. The lane gate 312 may return to an idle position along a longitudinal axis of the cross-over bridge 309. Alternatively, the lane gate 312 may sit idle at position 6 until a next transport element need to be picked up by the rotatable disc 310.

According to various embodiments, the laboratory product transport element presence sensors 320 and 322 may detect the arrival of the first and second laboratory product transport elements 304 and 306 at positions 1 and 2, respectively, when the sensors 320 and 322 detect the leading edge of the laboratory product transport elements 304 and 306. The laboratory product transport element presence sensors 320 and 322 may also detect when the first and second laboratory product transport elements 304 and 306 are coupled to the rotatable disc 310 when the sensors 320 and 322 detect the trailing edge of the laboratory product transport elements 304 and 306.

According to various embodiments, the sensors 326 and 328 may detect the release of the first and second laboratory product transport elements 304 and 306 at positions 3 and 4, respectively. The sensors 326 and 328 may notify the control logic (i.e. controller) when the laboratory product transport element is clear of the rotatable disc so that the next laboratory product transport element can be processed (i.e. moved). The sensors 326 and 328 may also notify the control logic when there is queue at positions 3 and/or 4 so that the system will cease processing (i.e. moving) any more laboratory product transport elements until the queue is cleared.

Figure 4A:
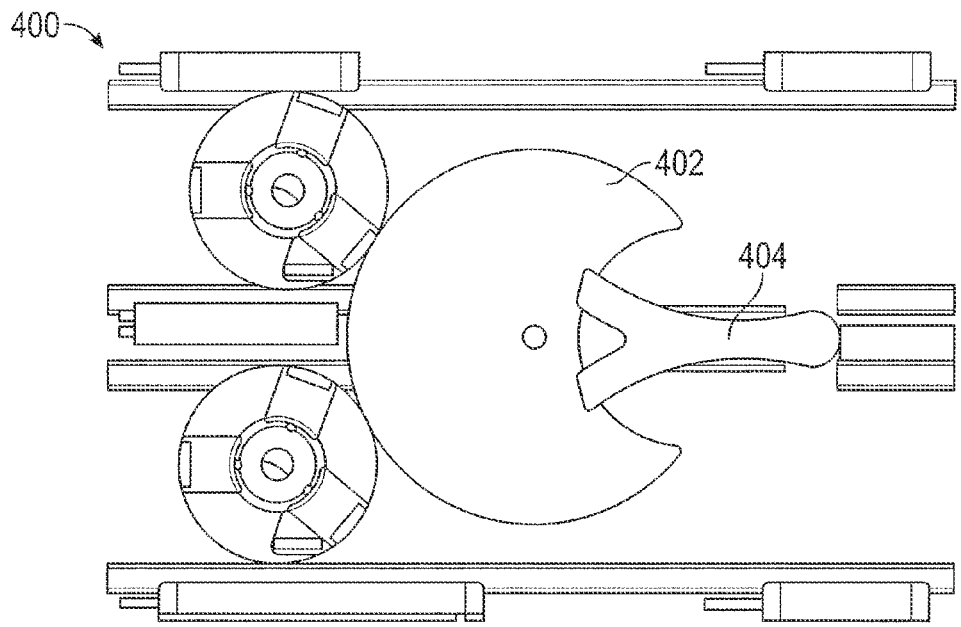
FIGS. 4A-4D show home positions and relative movements of a rotatable disc and a lane gate of an exemplary transport system, according to an exemplary embodiment.
Figure 4B:
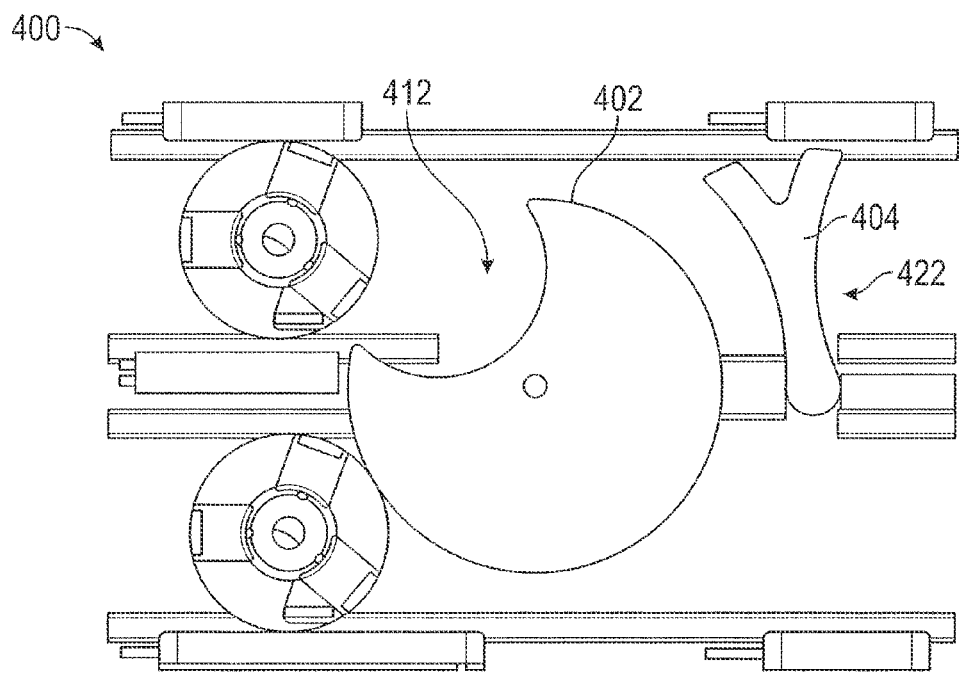
Figure 4C:
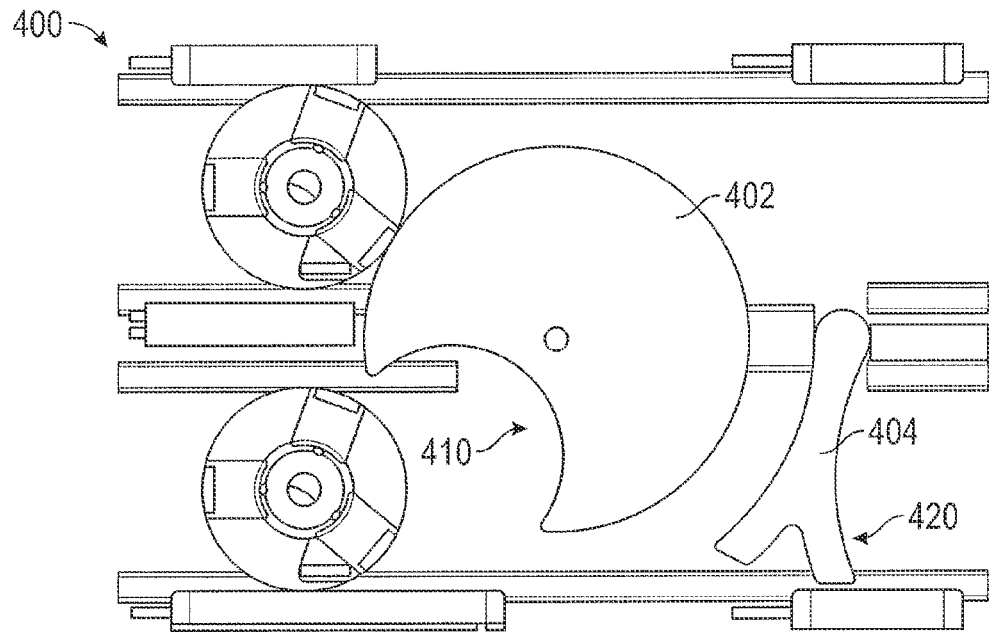
Figure 4D:
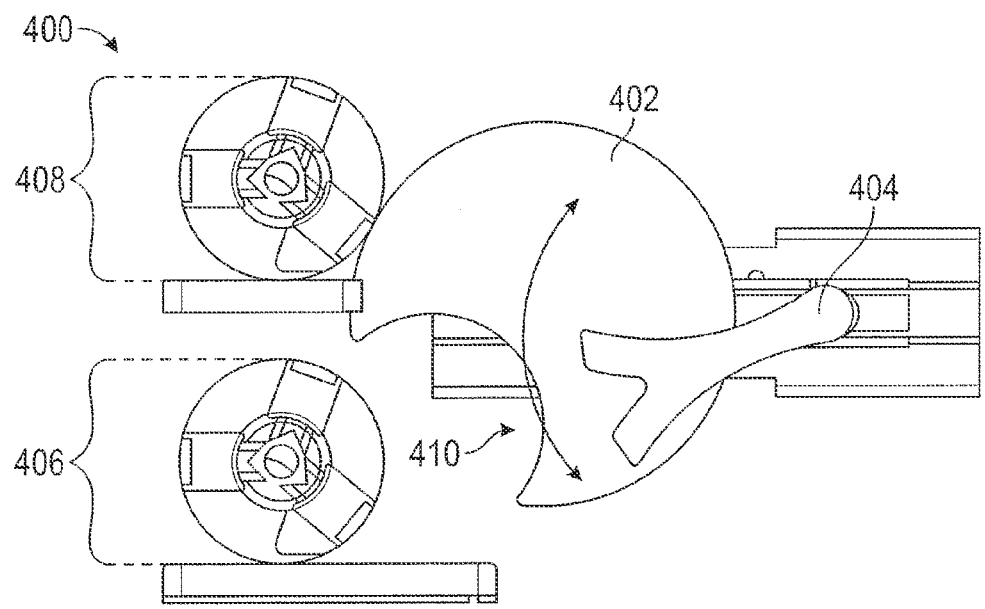

As discussed above, the rotatable disc and the lane gate may have idle positions. In some embodiments, the rotatable disc and the lane gate may also have a home position. The home position may be the same as the idle position. Alternatively, the home position may be different from the idle position. FIG. 4A illustrates a possible home positions of the rotatable disc and the lane gate, in case of a transport element movement from the left to the right side. FIGS. 4B-4D illustrate the relative movements of the rotatable disc 402 and the lane gate 404 of an exemplary transport system 400.

FIG. 4A illustrates the home position for the rotatable disc 402 and the lane gate 404. In some embodiments, the home position of the lane gate 404 may be the same as the idle position discussed above in connection with FIG. 2. That is, in the home position of the lane gate 404, the longitudinal axis of the lane gate 404 may be oriented parallel to the movement direction of the transport elements. At the home position of the lane gate 404, the longitudinal axis of the lane gate 404 may be in between the two same-direction movable conveyor lanes. According to various embodiments, there may be an initialization (i.e. homing) step, wherein the rotatable disc 402 and the lane gate 404 are moved into a homing position before the movement of the movable conveyor lanes of the transport system is started. This shall prevent that a laboratory product transport element is unintentionally entering the opening of the rotatable disc during the homing sequence of the rotatable disc and the lane gate.

In various embodiments, the rotatable disc 402 may have hard stop positions. For example, the hard stop positions of the rotatable disc 402 may be provided at laboratory product transport element entrance positions 410 and 412. The laboratory product transport element entrance positions 410 and 412 may be defined as positions on the first movable conveyor lane 406 or the second movable conveyor lane 408, respectively, where the laboratory product transport element enters the opening of the rotatable disc 402.

The lane gate 404 may also have hard stop positions. For example, the hard stop positions of the lane gate 404 may be provided at each intended lane transfer position 420 and 422. The intended lane transfer positions 420 and 422 may be defined as positions on the first movable conveyor lane 406 or the second movable conveyor lane 408, respectively, where the laboratory product transport element moves from the first movable conveyor lane 406 to the second movable conveyor lane 408, or vice versa. The hard stop positions may be provided either at or in close proximity of the sample transport element entrance positions such that the rotatable disc (or the lane gate) does not come to the hard stop position during normal operation.

For example, the rotatable disc 402 and the lane gate 404 may be at a first hard stop position, as illustrated in FIG. 4B. The rotatable disc 402 and the lane gate 404 may be at a second hard stop position, as illustrated in FIG. 4C. Once at a hard stop position, rotatable disc 402 and the lane gate 404 may not move any further, i.e. the hard stop poses an interference to prevent any further rotation or movement. Thus, the hard stop positions are used for the homing (i.e. initialization) sequence of the rotatable disc 402 and the lane gate 404. When the system is turned off, the controller may move the rotatable disc 402 and the lane gate 404 to the closest hard stop position. If the position of the rotatable disc 402 and the lane gate 404 is tempered with (e.g. the rotatable disc 402 and the lane gate 404 is manually moved) when the system is off, the controller will move the rotatable disc 402 and the lane gate 404 to the last hard stop position when the system is turned on again. During the initialization sequence, the rotatable disc 402 and the lane gate 404 may move in a given direction (clockwise or counter-clockwise) to arrive at (i.e. find) the first hard stop. The rotatable disc 402 and the lane gate 404 may move in the opposite direction to arrive at (i.e. find) the second hard stop. Both hard stop positions may be remembered and verified against a set predetermined encoder range to ensure that there is no obstruction in way of preventing correct initialization.

If the rotatable disc 402 is not carrying a laboratory product transport element, then the rotatable disc 402 may move faster between the two hard stop positions than when the rotatable disc 402 is carrying a laboratory product transport element.

FIG. 4D illustrates the movement of the rotatable disc 402 and the lane gate 404 between home position and hard stop positions. The lane gate 404 may move clockwise and counter-clockwise over the rotatable disc 402. The rotatable disc 402 moves toward the first movable conveyor lane 406 to accept the laboratory product transport element 410 in an opening of the rotatable disc 402. The lane gate 404 moves clockwise to block access to the second movable conveyor lane 408 or the lane gate 404 moves counter-clockwise to block access to the first movable conveyor lane 406, according to the destination of the laboratory product transport element 410 (e.g. the first movable conveyor lane 406 or the second movable conveyor lane 408, respectively).

Figure 5:
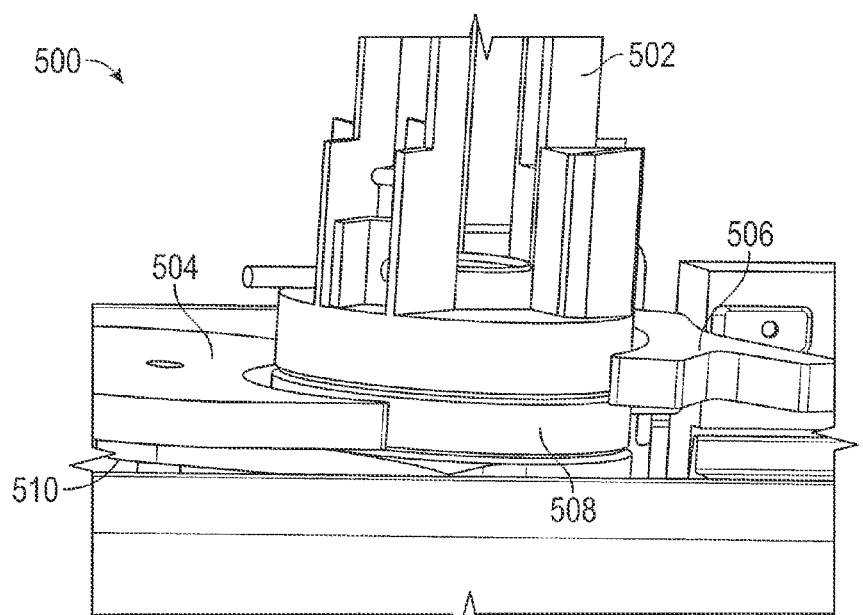
FIG. 5 shows a side view of an exemplary transport system where the rotatable disc interfaces with an exemplary laboratory product transport element, according to an exemplary embodiment.

The interfacing between the lateral opening of the rotatable disc and the laboratory product transport element should be such that the sample carried by the transport element should not be disturbed while being carried by the rotatable disc. FIG. 5 shows a side view of an exemplary transport system 500 where an opening of the rotatable disc 504 interfaces with an exemplary laboratory product transport element 502. A rotatable bearing surface 508 is provided at the bottom of the laboratory product transport element 502. The laboratory product transport element 502 may be traveling along a first moving path 510. If the laboratory product transport element 502 is to be moved to a second moving path, the lane gate 506 is moved to block access to the remainder of the first moving path 510. An opening of the rotatable disc 504 may interface with the bottom rotatable bearing surface 508 of the laboratory product transport element 502. The rotatable bearing surface 508 allows the rotatable disc 504 to move the laboratory product transport element 502 without disturbing the sample carried therein. The use of the rotatable bearing surface is provided for illustrative purposes only and should not be construed as limiting. Other types of coupling which would allow to maintain the orientation of the laboratory product transport element are considered to be within the scope of the present application. For example the laboratory product transport element 502 may have a smooth and basically abrasion-proof surface in the area where the laboratory product transport element 502 is interfacing with the opening of the rotatable disc.

According to various embodiments, the laboratory product transport elements may be orientation-specific laboratory product transport elements. When an orientation-specific laboratory product transport element is used, the orientation of the laboratory product transport element with respect to the conveyor lanes should remain unchanged. Accordingly, the coupling between the rotatable disc and the orientation-specific laboratory product transport element should be such that the orientation of the orientation-specific laboratory product transport element is not changed, even if the orientation-specific laboratory product transport element is transferred to another lane. This can be achieved by including structural features on the orientation-specific laboratory product transport element and within the opening of the rotatable disc such that the orientation-specific laboratory product transport element is not capable of performing a free rotation while interacting with the opening of the rotatable disc.

In some embodiments, an RFID (radio frequency ID) reader may read information associated with a laboratory product, which is stored on a RFID tag, located either on the laboratory product or on the transport element. For example, a transport element sensor may detect the orientation of the orientation-specific laboratory product transport elements by reading RFID tags or reflective films that may be attached to the orientation-specific laboratory product transport elements. In some embodiments, the different RFID tags may be provided on both sides of an orientation-specific laboratory product transport element. An orientation detection may be performed by reading the RFID tags with the RFID readers.

Exemplary transport systems with two parallel same-direction lanes are discussed above. However, the present invention is not limited to parallel same-direction two-lane systems. In some embodiments, multiple-lane transport systems, such as four-lane transport systems, may be used along with an end-of-lane transport system to carry the laboratory product transport elements between the lanes. An end-of-lane transport system may be used to change the direction of movement of a transport element by guiding the transport element to a different lane, e.g. being oriented or moving in a direction opposite to the original direction of movement of the transport element. If the end-of-lane transport system is located between a first lane, moving in a first direction and a second lane, moving in the opposite direction, the transport element can be guided through an opening provided between the first lane and the second lanes. The end-of-lane transport system may comprise a rotatable disc with at least one lateral opening, capable of accepting the transport element arriving at a first lane, and a deflection element, capable of preventing the transport element from leaving the lateral opening of the rotatable disc during the rotation of the rotatable disc, unless the transport element has reached a second lane on which it is scheduled to continue its travel. The rotatable disc of an end-of-lane transport element may comprise multiple lateral openings in order to increase throughput. End-of-lane transport systems may be located at the end of a lane or at any suitable place of a multi-lane transport system, where a change of direction of movement of transport elements is desired. Other alternative multiple-lane transport systems may include at least one input lane and a plurality of output lanes formed at pre-determined angles with the at least one input lane.

In some embodiments, more than one input lane may arrive at a rotatable disc/lane gate combination either parallel to each other or in defined angels to each other, e.g. in a 90° angle. A first lane gate may be constructed to alternatively block a first or a second output lane. The system may comprise additional lane gate(s) that are configured to flip between a position where the access to an additional output lane is blocked, and a non-blocking position, where the access to said output lane is granted.

Figure 6:
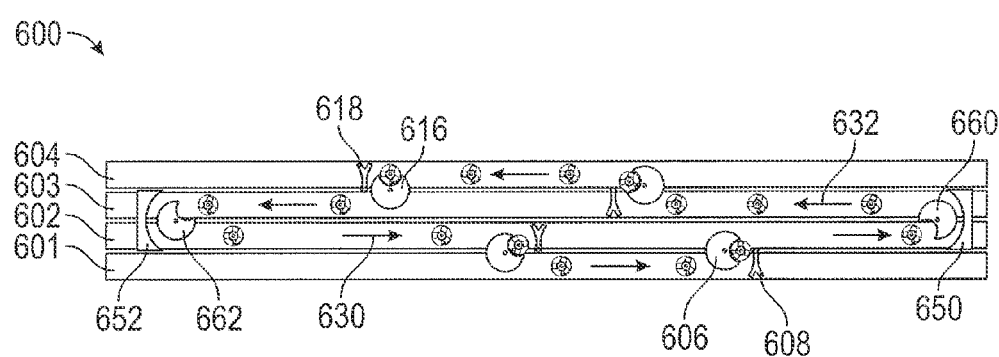
FIG. 6 shows an exemplary four-lane transport system coupled to end-of-lane transport systems, according to an exemplary embodiment.

FIG. 6 shows an exemplary four-lane transport system 600 comprising end-of-lane transport systems 650 and 652, according to an exemplary embodiment. The four-lane transport system 600 may include a first movable conveyor lane 601 and a second movable conveyor lane 602 moving in a first direction 630. The four-lane transport system 600 may also include a third movable conveyor lane 603 and a fourth movable conveyor lane 604 moving in a second direction 632 opposite to the first direction 630. The four-lane transport system 600 may also include a plurality of transfer systems each having a rotatable disc and a lane gate. For example, the four-lane transport system 600 may include a first rotatable disc 606 and a first lane gate 608 for transferring the laboratory product transport elements traveling along the first movable conveyor lane 601 and the second movable conveyor lane 602 between the first movable conveyor lane 601 and the second movable conveyor lane 602. The first lane gate 608 is provided downstream from (i.e. after) the first rotatable disc 606 in the first direction 630.

The four-lane transport system 600 may also include a second rotatable disc 616 and a second lane gate 618 for transferring the laboratory product transport elements traveling along the third movable conveyor lane 603 and the fourth movable conveyor lane 604 between the third movable conveyor lane 603 and the fourth movable conveyor lane 604. The second lane gate 618 is provided downstream from (i.e. after) the second rotatable disc 616 in the second direction.

The first rotatable disc 606 and the first lane gate 608 function together to move the laboratory product transport elements from the first movable conveyor lane 601 and the second movable conveyor lane 602 to the second movable conveyor lane 602, as discussed above in connection with FIGS. 2-3B3. Specifically, while the first lane gate 608 blocks access to the remainder to the first movable conveyor lane 601, the first rotatable disc 606 carries the laboratory product transport elements from either the first movable conveyor lane 601 or the second movable conveyor lane 602 to the second movable conveyor lane 602.

At the end of the second movable conveyor lane 602, the end-of-lane transport system 650 moves the laboratory product transport elements from the second movable conveyor lane 602 to the third movable conveyor lane 603. The end-of-lane transport system 650 includes a third rotatable disc 660 which interfaces with the laboratory product transport elements to move the laboratory product transport elements from the second movable conveyor lane 602 to the third movable conveyor lane 603. According to the exemplary configuration illustrated in FIG. 6, the third rotatable disc 660 may rotate counter-clockwise when carrying the laboratory product transport elements to maintain the orientation of the laboratory product transport elements and to reduce sample perturbation, if possible.

The second rotatable disc 616 and the second lane gate 618 function together to move the laboratory product transport elements from the third movable conveyor lane 603 and the fourth movable conveyor lane 604 to the third movable conveyor lane 603, as discussed above in connection with FIGS. 2-3B3. Specifically, while the second lane gate 618 blocks access to the remainder to the fourth movable conveyor lane 604, the second rotatable disc 616 carries the laboratory product transport elements from the fourth movable conveyor lane 604 to the third movable conveyor lane 603.

At the end of the third movable conveyor lane 603, the end-of-lane transport system 652 moves the laboratory product transport elements from the third movable conveyor lane 603 to the second movable conveyor lane 602. The end-of-lane transport system 652 includes a fourth rotatable disc 662 which interfaces with the laboratory product transport elements to move the laboratory product transport elements from the third movable conveyor lane 603 to the second movable conveyor lane 602. According to the exemplary configuration illustrated in FIG. 6, the fourth rotatable disc 662 may rotate counter-clockwise when carrying the laboratory product transport elements to maintain the orientation of the laboratory product transport elements and to reduce sample perturbation, if possible.

Figure 7:
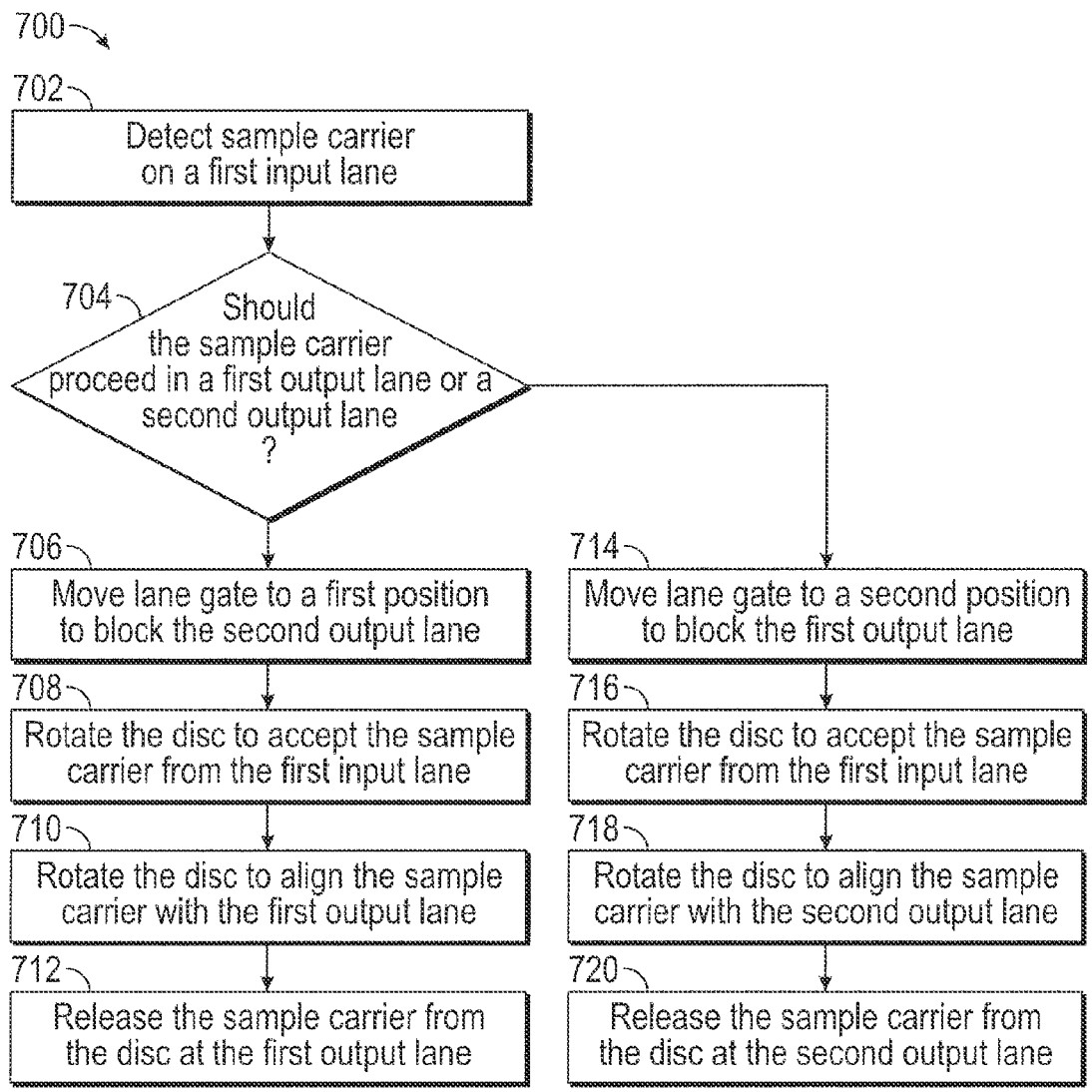
FIG. 7 shows a flow diagram of a method for transporting a laboratory product transport element between two same-direction movable conveyor lanes, according to an exemplary embodiment.

FIG. 7 shows a flow diagram 700 of a method for transporting a laboratory product transport element in a multi-lane laboratory product transport system including at least first input lane, a first output lane and a second output lane. The method starts with detecting the arrival of a first laboratory product transport element on a first movable conveyor input lane (step 702). It is determined whether the laboratory product transport element is scheduled to proceed on a first movable conveyor output lane or a second movable conveyor output lane (step 704). If it is determined that the laboratory product transport element should continue traveling on the first movable conveyor output lane, the lane gate is moved to a first position to block access to the second movable conveyor output lane (step 706). The rotatable disc is rotated to accept the laboratory product transport element from the first input lane (step 708). The rotatable disc may accept the laboratory product transport element in an opening of the rotatable disc. The rotatable disc is rotated clockwise or counter-clockwise to align the laboratory product transport element with the first movable conveyor output lane (step 710). Once aligned, the rotatable disc releases the laboratory product transport element on the first movable conveyor output lane (step 712).

If it is determined that the laboratory product transport element should move to the second movable conveyor output lane, the lane gate is moved to a second position to block access to the first movable conveyor output lane (step 714). The rotatable disc is rotated to accept the laboratory product transport element from the first input lane (step 716). The rotatable disc may accept the laboratory product transport element in an opening of the rotatable disc. The rotatable disc is rotated clockwise or counter-clockwise to align the laboratory product transport element with the second movable conveyor output lane (step 718). Once aligned, the rotatable disc releases the laboratory product transport element on the second movable conveyor output lane (step 720).

The various components shown in FIGS. 2-6 may be controlled by a control software to perform the method illustrated in FIG. 7. The control software may run one or more computer apparatuses (e.g., a server computer) to facilitate the functions described herein. Examples of such subsystems or components of the one or more computer apparatuses are shown in FIG. 8.

Figure 8:
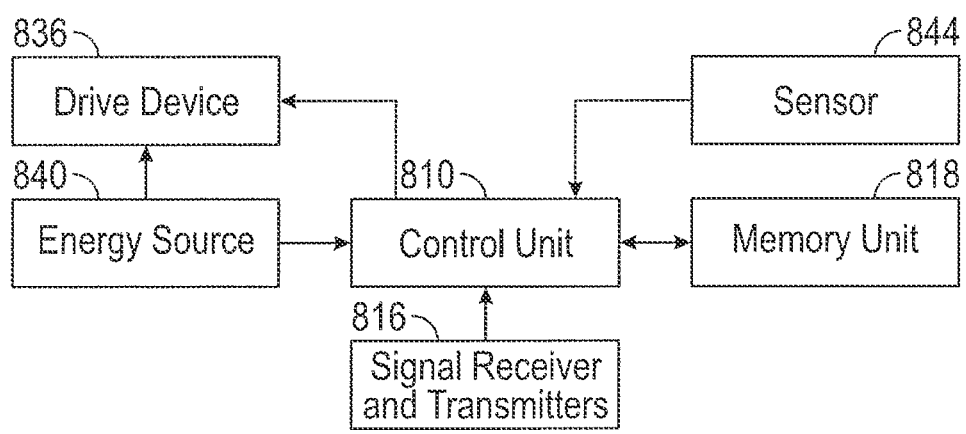
FIG. 8 shows an exemplary computer system according to embodiments of the present invention.

FIG. 8 shows a block diagram of some components in a laboratory product transport system according to an embodiment of the invention. Many of the components in FIG. 8 are already described in detail above, and the descriptions above are herein incorporated by references. FIG. 8 shows a central control unit 810, which may be in the form of one or more processors such as one or more microprocessors. The central control unit 810 may include a control mechanism to control the movement of various elements of the control system described above. A memory unit 818 may be coupled to the control unit 810. The memory unit 818 may comprise and store code, executable by the processor in the control unit 810 to perform any of the functions described above, including but not limited to positioning and rotation of the rotatable disc and the lane gate.

An energy source 840 (e.g., an energy accumulator and/or an energy receiver) may provide power to a drive device 836 (e.g., a motor). The energy source 840 and one or more drive devices 836 may allow the movement of the movable conveyor lanes (e.g. chains or belt conveyors), the movement of the rotatable disc and the movement of the lane gate described above.

In order to communicate with its external environment, one or more sensors 844 may be operatively coupled to the control unit 810, and one or more signal receivers and transmitters 816 can be coupled to the control unit 810. The sensors 844 may communicate with devices such as near field communication devices on a transfer path. For example, the sensors 844 may include the thru beam sensors and the laboratory product transport element presence sensors discussed above. The signal receiver(s) 816 receive control and/or drive signals for the laboratory product transport element from a host control system. The signal transmitters 816 can transmit signals to the host control system regarding its status (e.g., its internal status, its status with respect to other laboratory product transport elements, etc.).

Specific details regarding some of the above-described aspects are provided below. The specific details of the specific aspects may be combined in any suitable manner without departing from the spirit and scope of embodiments of the invention.

Storage media and computer readable media for containing code, or portions of code, may include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, data signals, data transmissions, or any other medium which may be used to store or transmit the desired information and which may be accessed by the computer. Based on the disclosure and teachings provided herein, a person of ordinary skill in the art may appreciate other ways and/or methods to implement the various embodiments.

Based on the disclosure and teachings provided herein, a person of ordinary skill in the art may know and appreciate other ways and/or methods to implement the present invention using hardware and a combination of hardware and software Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

The above description is illustrative and is not restrictive. Many variations of the invention may become apparent to those skilled in the art upon review of the disclosure. The scope of the invention should, therefore, be determined not with reference to the above description, but instead should be determined with reference to the pending claims along with their full scope or equivalents.

One or more features from any embodiment may be combined with one or more features of any other embodiment without departing from the scope of the invention.

A recitation of "a", "an" or "the" is intended to mean "one or more" unless specifically indicated to the contrary.

What is claimed is:

1. An apparatus for use with transport lanes including at least one input lane, a first output lane and a second output lane, the apparatus comprising:
a rotatable disc provided between the first output lane and the second output lane, wherein:
the rotatable disc includes at least one lateral opening interfaceable with a transport element traveling on the at least one input lane, wherein the lateral opening has a pre-determined negative curvature, and
an axis of rotation of the rotatable disc is perpendicular to a top surface of the first output lane and the second output lane; and
a lane gate provided adjacent to the rotatable disc, wherein:
the lane gate is pivotable to block access of the transport element to the first output lane or the second output lane.

2. The apparatus of claim 1, wherein:
an outer peripheral surface of the rotatable disc has a positive curvature; and
the lane gate comprises elongated sides having a negative curvature corresponding to the positive curvature of the rotatable disc such that the lane gate is cooperatively structured with the rotatable disc.

3. The apparatus of claim 1, wherein the rotatable disc is provided at a higher position than the lane gate such that the lane gate is pivotable below the rotatable disc.

4. The apparatus of claim 1, wherein the rotatable disc is provided at a lower position than the lane gate such that the lane gate is pivotable above the rotatable disc.

5. The apparatus of claim 1, wherein the lateral opening has a pre-determined negative curvature corresponding to the positive curvature of the transport element traveling on the at least one input lane.

6. The apparatus of claim 1, wherein the at least one input lane, the first output lane and the second output lane are movable conveyor lanes.

7. The apparatus of claim 1, wherein:
the rotatable disc is rotatable to accept, at the lateral opening of the rotatable disc, the transport element traveling on the first input lane,
the lane gate is controllable to unblock an output lane based on a predetermined travel path of the transport element, and
the rotatable disc is rotatable to transport the transport element to the output lane and release the transport element from the lateral opening to the output lane.

8. A transport system comprising:
a multi-lane transport arrangement including at least one input lane, a first output lane and a second output lane;
a rotatable disc provided at an end of the at least one input lane and at a beginning of the first output lane and the second output lane, wherein:
the rotatable disc includes at least one lateral opening interfaceable with a transport element traveling on the at least one input lane, wherein the lateral opening has a pre-determined negative curvature, and
an axis of rotation of the rotatable disc is perpendicular to a top surface of the first output lane and the second output lane;
a lane gate provided adjacent to the rotatable disc, wherein:
the lane gate is pivotable to block access of the transport element to the first output lane or the second output lane depending on a pre-determined travel path of the transport element; and
a controller programmed to control a movement of the rotatable disc and the lane gate to guide the transport element through the multi-lane transport arrangement along the pre-determined travel path.

9. The system of claim 8, wherein:
an outer peripheral surface of the rotatable disc has a positive curvature; and
the lane gate comprises elongated sides having a negative curvature corresponding to the positive curvature of the rotatable disc such that the lane gate is cooperatively structured with the rotatable disc.

10. The system of claim 8, wherein the rotatable disc is provided at a higher position than the lane gate such that the lane gate pivots below the rotatable disc.

11. The system of claim 8, wherein the rotatable disc is provided at a lower position than the lane gate such that the lane gate pivots above the rotatable disc.

12. The system of claim 8, wherein the rotatable disc is sized and dimensioned such that the transport element is prevented from moving forward on the first output lane or the second output lane unless the transport element is located in the at least one lateral opening of the rotatable disc and the lateral opening of the rotatable disc is aligned with the first output lane or the second output lane.

13. The system of claim 8, further comprising:
a cross-over bridge portion provided between the first output lane and the second output lane, wherein the cross-over bridge portion supports the transport element while the rotatable disc moves the transport element over the cross-over bridge portion to the first output lane or the second output lane.

14. The system of claim 8, wherein the second output lane is parallel to the first output lane.

15. The system of claim 8, wherein a rotation speed of the rotatable disc when carrying the transport element is slower than a rotation speed when moving without the transport element.

16. The system of claim 8, wherein the at least first input lane, the first output lane and the second output lane are movable conveyor lanes.

17. The system of claim 8, further comprising:
a second input lane,
wherein the first input lane and the first output lane are configured as a first continuous lane movable below the rotatable disc, and
wherein the second input lane and the second output lane are configured as a second continuous lane movable below the rotatable disc.

18. A method for controlling the movement of a transport element within a multi-lane transport system, the multi-lane transport system including a first input lane, a second input lane, a first output lane, a second output lane, a rotatable disc with at least one lateral opening for receiving the transport element and a lane gate for selectively blocking access to the first output lane or the second output lane, the method comprising:
detecting the transport element on the first input lane;

moving the lane gate to block access to one of the first output lane and the second output lane, wherein the first input lane and the first output lane are configured as a first continuous lane movable below the rotatable disc, and wherein the second input lane and the second output lane are configured as a second continuous lane movable below the rotatable disc;

rotating the rotatable disc to a position where the lateral opening of the rotatable disc faces the detected transport element;

receiving the detected transport element in the lateral opening of the rotatable disc;

rotating the rotatable disc to align the transport element with the other one of the first output lane and the second output lane; and releasing the transport element from the lateral opening of the rotatable disc on the other one of the first output lane and the second output lane.

19. The method of claim 18, further comprising:

determining whether the transport element is assigned a pre-determined route on the first output lane or the second output lane; and moving the lane gate to unblock the first output lane or the second output lane based on the determining.

20. The method of claim 18, wherein the lane gate is at least temporarily moved simultaneously with rotating the rotatable disc.

21. The method of claim 18, wherein:

the transport element is passively transported by the movement of the first input lane towards the rotatable disc, the transport element is moved to the first output lane or the second output lane by the rotation of the rotatable disc, and the transport element is passively transported by the movement of the first output lane or the second output lane.

22. The method of claim 21, wherein the transport element is moved by the rotation of the rotatable disc past said first output lane to the second output lane when the first output lane is blocked by the lane gate, and the transport element is moved by the rotation of the rotatable disc past the second output lane to the first output lane when the second output lane is blocked by the lane gate.

23. An apparatus for use with transport lanes including at least one input lane, a first output lane and a second output lane, the apparatus comprising:

a rotatable disc provided between the first output lane and the second output lane, wherein:

the rotatable disc includes at least one lateral opening interfaceable with a transport element traveling on the at least one input lane, and an axis of rotation of the rotatable disc is perpendicular to a top surface of the first output lane and the second output lane; and a lane gate provided adjacent to the rotatable disc, wherein:

the lane gate is pivotable to block access of the transport element to the first output lane or the second output lane, and wherein the lane gate is dimensioned such that, at a neutral position, the lane gate blocks neither the first output lane nor the second output lane.

24. An apparatus for use with transport lanes including at least one input lane, a first output lane and a second output lane, the apparatus comprising:

a rotatable disc provided between the first output lane and the second output lane, wherein:

the rotatable disc includes at least one lateral opening interfaceable with a transport element traveling on the at least one input lane, and an axis of rotation of the rotatable disc is perpendicular to a top surface of the first output lane and the second output lane; and a lane gate provided adjacent to the rotatable disc, wherein:

the lane gate is pivotable to block access of the transport element to the first output lane or the second output lane, and wherein the first output lane branches off of the at least one input lane at a first angle and the second output lane branches off of the at least one input lane at a second angle.

* * * * *